United States Patent
Krahwinkel et al.

(10) Patent No.: US 10,123,806 B2
(45) Date of Patent: Nov. 13, 2018

(54) CONTROL APPARATUS AND CONTROL SYSTEM FOR A TOURNIQUET DEVICE

(71) Applicant: ulrich GmbH & Co. KG, Ulm (DE)

(72) Inventors: Martin Krahwinkel, Ulm (DE); Armin Hänsler, Laupheim (DE); Sven Erdmann, Ulm (DE)

(73) Assignee: ULRICH GMBH & CO. KG, Ulm (DE)

( * ) Notice: Subject to any disclaimer, the term of this patent is extended or adjusted under 35 U.S.C. 154(b) by 607 days.

(21) Appl. No.: 14/442,153

(22) PCT Filed: Nov. 12, 2013

(86) PCT No.: PCT/EP2013/073561
§ 371 (c)(1),
(2) Date: May 12, 2015

(87) PCT Pub. No.: WO2014/072520
PCT Pub. Date: May 15, 2014

(65) Prior Publication Data
US 2016/0270795 A1  Sep. 22, 2016

(30) Foreign Application Priority Data

Nov. 12, 2012 (DE) .......................... 10 2012 110 827

(51) Int. Cl.
*A61B 17/135* (2006.01)
*A61B 5/021* (2006.01)
(Continued)

(52) U.S. Cl.
CPC ...... *A61B 17/1355* (2013.01); *A61B 5/02141* (2013.01); *A61B 17/1322* (2013.01);
(Continued)

(58) Field of Classification Search
CPC . A61B 17/132; A61B 17/1322; A61B 17/135; A61B 17/1355;
(Continued)

(56) References Cited

U.S. PATENT DOCUMENTS 4,106,002 A * 8/1978 Hogue, Jr. ............. A61B 5/022
340/573.1
4,469,099 A * 9/1984 McEwen ............ A61B 17/1355
600/495
(Continued)

FOREIGN PATENT DOCUMENTS

AT            59275 B      7/1991
DE         4008711 A1      9/1990
(Continued)

OTHER PUBLICATIONS

International Preliminary Report on Patentability dated May 12, 2015 for PCT/EP2013/073561.
(Continued)

*Primary Examiner* — Ryan J Severson
(74) *Attorney, Agent, or Firm* — Paul D. Bianco; Katherine Davis; Fleit Gibbons Gutman Bongini & Bianco, PL (57) ABSTRACT

A control apparatus for a tourniquet device, to which tourniquet device a first compression cuff and/or at least one second compression cuff can be connected, with the compression cuffs having different volumes. The tourniquet device has an inflation apparatus for inflating the connected compression cuff. In order to present a tourniquet apparatus that enables the most efficient and in particular fast inflation of the tourniquet cuff possible and at the same time the most error-free operation of the tourniquet apparatus possible, a parameter set for controlling an inflation process of the respective compression cuff is associated with each compression cuff and is stored in a data memory of the control
(Continued)

apparatus. The parameter set associated with each compression cuff depends on the volume of the compression cuff. A method for controlling a tourniquet device and a control system for controlling a tourniquet apparatus having a tourniquet device that has an inflation apparatus and a control apparatus and having a compression cuff that can be applied to a limb and connected to the inflation apparatus.

10 Claims, 5 Drawing Sheets

(51) Int. Cl.
 *A61B 17/132* (2006.01)
 *A61B 90/90* (2016.01)
 *A61B 17/00* (2006.01)
(52) U.S. Cl.
 CPC ..... *A61B 90/90* (2016.02); *A61B 2017/00544* (2013.01); *A61B 2017/00557* (2013.01)
(58) Field of Classification Search
 CPC ...... A61B 2017/00557; A61B 5/02141; A61B 5/022; A61B 5/02208; A61B 5/02216; A61B 5/02225; A61B 5/02233; A61B 5/02241; A61B 5/0225; A61B 5/02255
 See application file for complete search history.

(56) References Cited

U.S. PATENT DOCUMENTS

| | | | | |
|---|---|---|---|---|
| 4,479,494 A * | 10/1984 | McEwen | ............ | A61B 5/02141 600/495 |
| 4,501,280 A | 2/1985 | Hood, Jr. | | |
| 4,520,819 A * | 6/1985 | Birmingham | ...... | A61B 17/1355 606/202 |
| 4,520,820 A * | 6/1985 | Kitchin | .............. | A61B 17/1355 606/202 |
| 4,548,198 A * | 10/1985 | Manes | ................ | A61B 17/1355 606/202 |
| 4,671,290 A * | 6/1987 | Miller | ................ | A61B 5/02225 600/494 |
| 4,691,738 A * | 9/1987 | McCune | ............ | A61B 17/1355 137/595 |
| 5,048,536 A * | 9/1991 | McEwen | .................. | A61B 5/03 600/561 |
| 5,060,654 A | 10/1991 | Malkamäki et al. | | |
| 5,181,522 A * | 1/1993 | McEwen | .................. | A61B 5/03 600/561 |
| 5,607,447 A * | 3/1997 | McEwen | ............. | A61B 5/1106 606/202 |
| 5,626,142 A * | 5/1997 | Marks | ................ | A61B 5/02141 600/492 |
| 5,842,996 A | 12/1998 | Gruenfeld et al. | | |
| 5,855,589 A * | 1/1999 | McEwen | ............. | A61B 5/02141 600/499 |
| 5,911,735 A * | 6/1999 | McEwen | ............. | A61B 5/1106 606/201 |
| 5,931,853 A * | 8/1999 | McEwen | ............ | A61B 17/1355 606/203 |
| 6,213,939 B1 * | 4/2001 | McEwen | ............ | A61B 17/1355 600/202 |
| 6,299,629 B1 | 10/2001 | Gruenfeld et al. | | |
| 6,450,966 B1 | 9/2002 | Hanna | | |
| 6,682,547 B2 * | 1/2004 | McEwen | ............. | A61B 17/135 356/425 |
| 7,226,419 B2 * | 6/2007 | Lane | .................... | A61B 5/0225 600/490 |
| 7,331,977 B2 * | 2/2008 | McEwen | ............. | A61B 17/135 606/202 |
| 8,235,922 B2 * | 8/2012 | Rowe | ................... | A61B 17/135 601/151 |
| 2003/0036771 A1 * | 2/2003 | McEwen | ............... | A61B 17/135 606/202 |
| 2003/0093001 A1 * | 5/2003 | Martikainen | .......... | A61B 5/022 600/499 |
| 2003/0167070 A1 * | 9/2003 | McEwen | ............... | A61B 17/135 606/203 |
| 2006/0293601 A1 | 12/2006 | Lane et al. | | |
| 2011/0046494 A1 | 2/2011 | Balji et al. | | |
| 2016/0270795 A1 * | 9/2016 | Krahwinkel | ....... | A61B 5/02141 |

FOREIGN PATENT DOCUMENTS

| | | |
|---|---|---|
| EP | 0122123 A2 | 10/1984 |
| JP | 2005261820 | 9/2005 |
| WO | 9306782 A1 | 4/1993 |
| WO | 9422364 A1 | 10/1994 |
| WO | 03015641 | 2/2003 |

OTHER PUBLICATIONS

International Search Report dated Apr. 11, 2014 for PCT/EP2013/073561 filed Nov. 12, 2013.
Result of examination report for DE 10 2012 110 827.7 filed Nov. 12, 2012.
English translation of Written Opinion for PCT/EP2013/073561, dated May 12, 2015.

* cited by examiner

CONTROL APPARATUS AND CONTROL SYSTEM FOR A TOURNIQUET DEVICE

FIELD OF THE INVENTION

The invention concerns a control apparatus for a tourniquet device, a method for the control of a tourniquet device with such a control apparatus, and a control system for the control of a tourniquet device.

BACKGROUND OF THE INVENTION

Tourniquet devices are used for the temporary regulation of the arterial blood flow in the upper and lower extremities of the human body or of an animal body. Known tourniquet devices comprise a tourniquet and a compression cuff that can be connected to it, which is placed on an extremity of a patient and is subsequently inflated so as to reduce the arterial blood flow in the extremity, perhaps to an absolute arrest of the blood flow. The duration and level of the pressure exerted on the extremity by the compression cuff are thereby set according to the specifications of the attending doctor. Typical fields of use for such tourniquet devices are the field of surgical and orthopedic operations, but also in anesthesia (IVRA, "Intravenous Regional Anesthesia").

The known tourniquet devices have an inflation apparatus for the inflation of the compression cuff connected to the tourniquet device and a control apparatus for the control of the inflation apparatus. So that a tourniquet device to bring about a control of blood flow to various extremities (for example, on the upper arm, on the forearm, on the thigh, or on the calf) and also on different patients can be used, compression cuffs of various sizes can be connected, as a rule, to a tourniquet device. Depending on the circumference of the extremity, a suitable compression cuff is selected, placed on the extremity, and inflated by means of the inflation apparatus of the tourniquet device to a prespecified pressure and over a prespecified duration of the control of the blood flow, so as to limit the blood flow in the extremity and to regulate it during the duration of the blood flow control. The various compression cuffs with different sizes can have a different volume and a different shape, so as to bring about as good as possible an adaptation to the size and shape of the extremity, the type of patient, and the operation procedure to be used.

From WO03/015,641 A1, a tourniquet device with a tourniquet instrument and a large number of tourniquet cuffs that can be connected to it are known, wherein the cuffs have different characteristics and, in particular, different cuff sizes, and each cuff is equipped with a cuff connector that comprises an identification device. The identification device thereby indicates the physical characteristics of the tourniquet cuff, in particular its cuff size. The tourniquet instrument comprises a detection device that is responsive to the identification device of the cuff when a cuff is connected to the tourniquet instrument, so as to detect the physical characteristics of the connected cuff. The identification device is a selection of predetermined colors, wherein each color corresponds to a predetermined physical characteristic of the cuff, for example, a specific cuff size. An optical detection device is located on the tourniquet instrument; it can determine the color of the identification device of a cuff and, in this way, can make a conclusion as to the type and the physical characteristics of the connected cuff. The identification of the physical characteristics of the connected cuff makes possible an optimization of different operating parameters and the emission of warning signals and the storage of operating data. Moreover, the automatic cuff identification prevents an erroneous connection of an unsuitable cuff to the tourniquet instrument.

In practical use, however, this known tourniquet device with an automatic cuff identification proves to be susceptible to error, because with the optical detection device, there may be an erroneous detection of the color of the identification device on the cuff connector. There is also the risk that a false identification device is installed on the cuff connector, which likewise leads to an erroneous identification of the cuff connected to the tourniquet instrument.

Via the automatic cuff identification, the known tourniquet device makes possible the optimization of different operating parameters and the emission of warning signals if an unsuitable cuff has been connected to the tourniquet instrument. An efficient operation of the tourniquet device, which is presented, for example, in as quickly as possible an inflation and release of the compression cuff connected to the tourniquet device, is, however, not yet brought about with the known tourniquet device.

SUMMARY OF THE INVENTION

Proceeding from this, a tourniquet device that brings about as efficient and, in particular, as quickly as possible an inflation of the tourniquet cuff and, at the same time, as error-free as possible an operation of the tourniquet device is disclosed in one embodiment.

Also disclosed are a control apparatus for a tourniquet device, a method for the control of a tourniquet device, and a control system of a tourniquet device.

The tourniquet device in accordance with the invention comprises a tourniquet device with an inflation apparatus and a control apparatus and a compression cuff, which can be connected to the inflation apparatus of the tourniquet device and can be placed on a limb, in particular in the area of the upper and lower extremities. The control apparatus contains a detection mechanism, with which the size and, in particular, the volume of the compression cuff connected to the inflation apparatus can be detected. The control apparatus controls the inflation apparatus for the inflation of the compression cuff by using a parameter set that is correlated with the size or the volume of the connected compression cuff.

Different compression cuffs with different cuff sizes or different volumes can be connected to the tourniquet device. The compression cuffs with different cuff sizes thereby form a cuff set correlated with the tourniquet device. Each compression cuff is thereby correlated with a parameter set for the control of an inflation process of this compression cuff and the parameter set is stored in a data storage unit of the tourniquet device. After detection of the size or the volume of the compression cuff connected to the tourniquet device by means of the detection mechanism, the control device selects the parameter set that is correlated with the connected compression cuff and controls the inflation apparatus using this parameter set, which is specifically coordinated with the size or the volume of the connected compression cuff. In this way, it is possible to have a very efficient inflation of the connected compression cuff in as short a time as possible, and it is possible to prevent the connected compression cuff from being inflated with a wrong pressure profile or an unsuitable end pressure.

With the detection mechanism for the detection of the volume or the size of the connected compression cuff, a pressure is preferably measured in the compression cuff and/or the flow rate of a pressure means that is pumped from the inflation apparatus into the compression cuff. The pressure means is appropriately compressed air or another compressed gas, such as nitrogen.

In a preferred embodiment example of the invention, in which the cuff size is detected with a pressure measurement, the control apparatus controls the inflation apparatus during the operation of the detection mechanism in such a way that it first inflates the connected compression cuff over a pre-specified detection period, using a first parameter set that is provided for the smallest compression cuff of the cuff set. After the expiration of the detection period, the pressure in the connected compression cuff is detected and passed on to the control apparatus. The control apparatus then determines, from the detected pressure, the size or the volume of the connected compression cuff and, finally, for the continued inflation of the cuff, selects the parameter set with which the cuff with the detected cuff volume is correlated. To this end, the control apparatus contains a data storage unit in which different parameter sets for the inflation of compression cuffs with different sizes or different volumes are stored. The parameter sets correlated with the different compression cuffs appropriately contain an inflation profile in the form of a pressure-time curve and a maximum pressure, which may not be exceeded during the inflation of the compression cuff. Appropriately, the parameter set of every compression cuff that can be connected to the tourniquet device also contains, moreover, a value for a maximum period that cannot be exceeded by the compression cuff in the inflated state. In this way, it is possible to ensure that blood flow control in the limb on which the compression cuff is placed, which is brought about by the inflated compression cuff, is not maintained over an excessively long period. Thus, damage can be avoided in the tissue of the limb, which may appear with an excessively long-lasting blood flow control.

BRIEF DESCRIPTION OF THE DRAWINGS

These and other advantages of the invention can be deduced from the exemplified embodiment described in more detail below, with reference to the accompanying drawings. The drawings show the following.

DETAILED DESCRIPTION OF PREFERRED EMBODIMENTS

Figure 1:
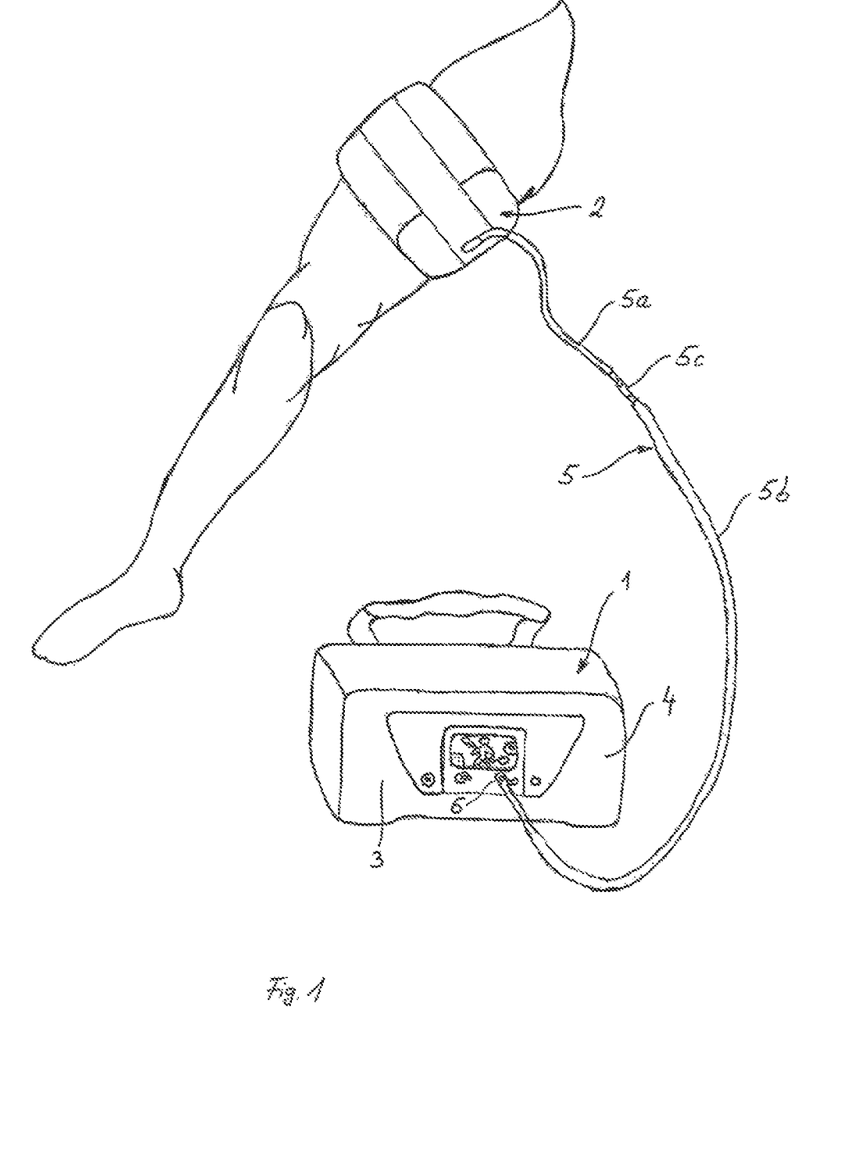
FIG. 1: Schematic depiction of a tourniquet device in accordance with the invention, which comprises a tourniquet device and a compression cuff which can be connected to it.

The schematic depiction of FIG. 1 shows a tourniquet apparatus with a tourniquet device 1 and a compression cuff 2 that is connected to it and which is placed on a limb of a patient. In the graphically depicted embodiment example, the inflatable compression cuff 2 is placed on an upper thigh of a patient. In a corresponding manner, the compression cuff can also be placed on other body extremities (for example, an arm), in order to provide a regulation of the arterial blood flow there, up to an absolute arrest of the blood flow. The tourniquet device 1 contains an inflation apparatus 3 and a control apparatus 4, which are located in a housing. The inflation apparatus 3 is coupled with the control apparatus 4 and is used for the inflation of the compression cuff 2, which is connected with the tourniquet device 1 via a connecting hose 5. The connecting hose 5 can be a compressed air hose, for example, a plastic hose. The connecting hose 5 can be made as one part or also in several parts with a first hose piece 5a, which is situated on the compression cuff 2, and a second hose piece 5b, wherein the two hose pieces 5a and 5b are connected with one another via a connecting piece 5c. An end of the connecting hose 5 is connected with a pressure means connection 6 of the tourniquet device 1. The other end of the connecting hose 5 is connected with an inflatable chamber of the compression cuff 2. For the inflation of the compression cuff 2, the inflation apparatus 3 of the tourniquet device 1 pumps the pressure means, for example, compressed air, through the connecting hose 5 into the compression cuff 2. The inflation apparatus 3 is thereby controlled by the control apparatus 4 so as to inflate the compression cuff 2 with a suitable inflation profile.

In this way, different compression cuffs with different sizes can be connected to the tourniquet device 1. Thus, in particular, a first compression cuff 2 can be connected to the tourniquet device 1, which is provided for the creation of a blood flow control on a limb with a large circumference, such as an upper thigh, and a second compression cuff with a smaller volume, which is suitable for the creation of a blood flow control on a limb with a smaller circumference, for example, an arm, can be connected to the tourniquet device 1. Appropriately, a set of compression cuffs with different sizes and, in particular, with different volumes can be correlated with the tourniquet device 1 so as to be able to select, for each intended application case, a suitable compression cuff with a suitable size. Such a set of compression cuffs can comprise, for example, three cuffs with different sizes or different volumes. The different cuff sizes can thereby be characterized, in a known manner, in accordance with their size, for example, with a letter codes "S" for a small cuff, "M" for a medium-size cuff, and "L" for a large cuff.

Each compression cuff (2S, 2M, 2L) of the cuff set is thereby correlated with a specific inflation profile. The inflation profile of each cuff is contained in a cuff-specific parameter set. The parameter sets for the individual compression cuffs of different sizes are deposited in a data storage unit of the control apparatus 4 of the tourniquet device 1. Appropriately, each parameter set that is correlated with a cuff with a specific size or with a specific volume contains an inflation profile in the form of a pressure-time curve and/or a time-dependent flow rate of the pressure means used for the inflation of the cuff. Moreover, the parameter set correlated with each compression cuff can contain a maximum value which may not be exceeded during the inflation of the individual compression cuff. Furthermore, the parameter set of each compression cuff can contain a value for a maximum blood flow control period which the compression cuff in the inflated state may not exceed. Each cuff with a specific volume is clearly correlated with a corresponding parameter set.

The control apparatus 4 integrated in the tourniquet device 1 contains a detection mechanism with which the size or the volume of the compression cuff 2 connected to the tourniquet device 1 can be detected. In a preferred embodiment example, the detection mechanism detects the size or the volume of the connected compression cuff 2 via a pressure measurement. In an alternative embodiment example, the detection of the size or the volume of the connected compression cuff 2 is also carried out by means of a flow rate measurement. Below, the details of these two implementation variants of the detection mechanism are also described individually.

The size of the connected compression cuff 2 detected by the detection mechanism or the volume of the connected compression cuff 2 detected by the detection mechanism is sent on to the control apparatus 4. With the aid of the detected size or the detected volume of the connected compression cuff 2, the control apparatus 4 selects the suitable parameter set for this cuff from the data storage unit in which the parameter sets for all connectable cuffs are deposited, and controls the inflation apparatus 3 using the selected parameter set. The inflation apparatus 3 pumps up the connected compression cuff in accordance with the selected parameter set and, in particular, in accordance with the inflation profile contained therein, so that it regulates the arterial blood flow in the limb on which it is placed.

Figure 2:
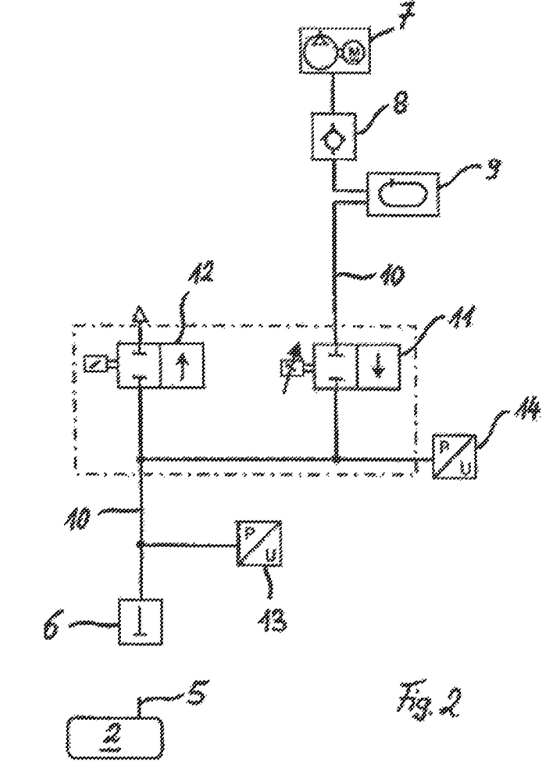
FIG. 2: pneumatic block diagram of a tourniquet device controlled in accordance with the invention, in a first embodiment.
Figure 3:
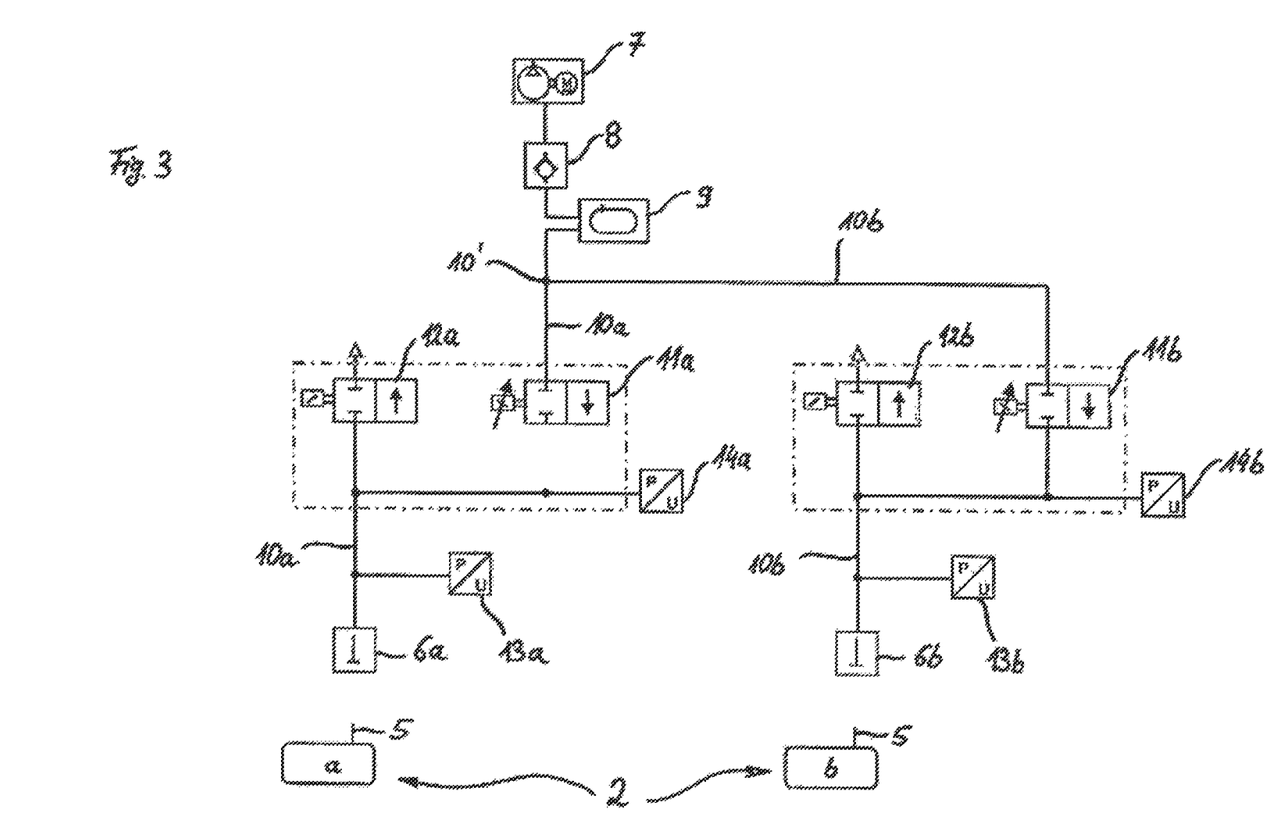
FIG. 3: pneumatic block diagram of a tourniquet device controlled in accordance with the invention, in a second embodiment.
Figure 4:
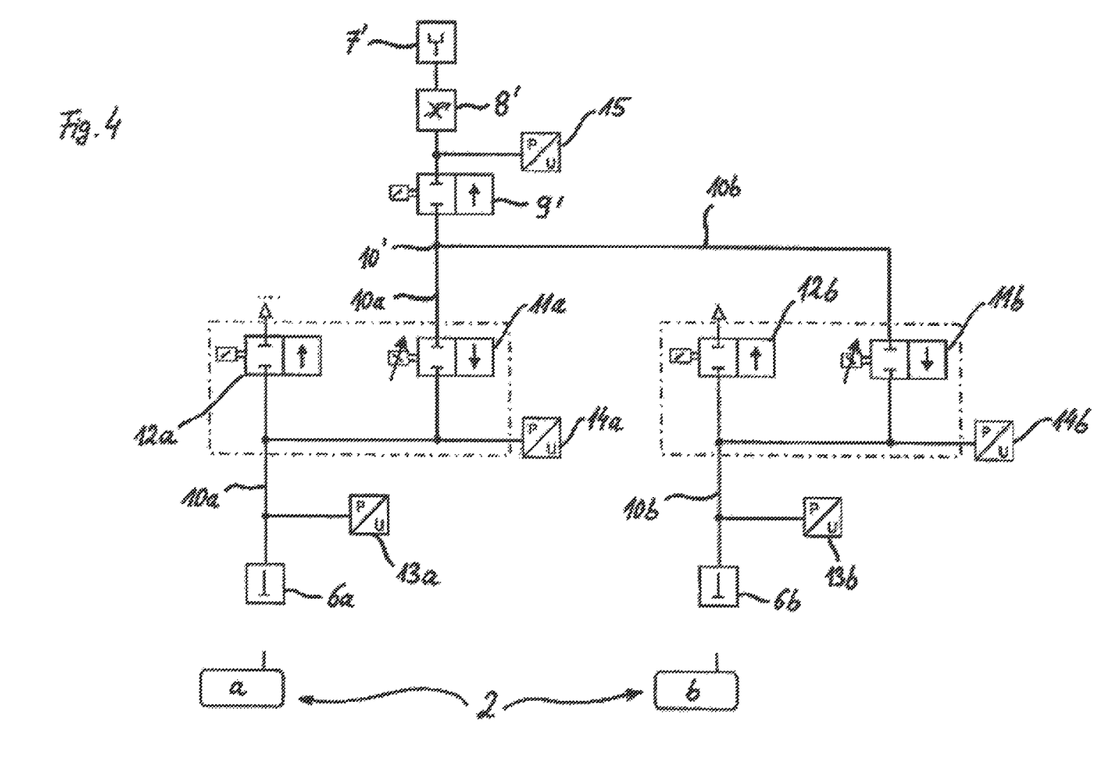
FIG. 4: pneumatic block diagram of a tourniquet device controlled in accordance with the invention, in a third embodiment.

FIGS. 2-4 show various embodiments of the tourniquet device 1 as pneumatic block diagrams. The embodiment shown in FIG. 2 shows a tourniquet device 1 with a one-channel inflation apparatus 3, which comprises a compressor 7. The compressor 7, which is supplied with energy via a power connection or a battery integrated into the tourniquet device 1, pumps a pressure means, in particular, compressed air, into a pressure means storage unit 9 via a non-return valve 8, and from there, via a pressure means conduit 10, to a connection 6 where the connecting hose 5 of a compression cuff 2 can be connected. A proportional valve 11 and a venting valve 12 are located in the pressure means conduit 10. The proportional valve 11 is used to regulate the pressure available at the connection 6. Via the venting valve 12, the pressure that builds up in the compression cuff 2 can be released so as to again cancel the blood flow control effected by the inflated compression cuff 2. The pressure made available at the connection 6 by the compressor 7 is detected by means of a pressure gauge 13. In the compression cuff 2 connected to the connection 6, this pressure corresponds to the cuff pressure. The proportional pressure after the proportional valve 11 is detected with another pressure gauge 14.

FIGS. 3 and 4 show two embodiment examples of a tourniquet device 1 with a two-channel inflation apparatus 3 in a pneumatic block diagram. Such tourniquet devices with a two-channel inflation apparatus can be used for the inflation of two-chamber cuffs. The two-channel tourniquet device 1 thereby contains two connections 6a, 6b for the connection of the two chambers a and b of a two-chamber cuff 2. Each connection 6a, 6b is correlated with a proportional valve 11a, 11b for the regulation of the pressure available at the individual connection, and a venting valve 12a, 12b. Accordingly, each connection 6a, 6b has a pressure gauge 13a, 13b for the detection of the chamber pressure of the chamber a, b of the cuff 2, connected at each connection. Each proportional valve 11a, 11b is also correlated with another pressure gauge 14a, 14b for the detection of the proportional pressure. As in the embodiment example of FIG. 2, the tourniquet 1 of the embodiment example of FIG. 3 also has a pressure means storage unit 9 and a compressor 7, and a non-return valve 8 located between the two, and a pressure means conduit 10, via which the pressure means is conducted from the pressure means storage unit 9 to the connections 6a and 6b. For the distribution of the pressure means stored in the pressure means storage unit 9 at the two connections 6a and 6b, a branching 10' into two pressure means conduits 10a and 10b is provided in the pressure means conduit 10 in the embodiment example of FIG. 3.

The embodiment example of tourniquet device 1 shown in FIG. 4 essentially corresponds to the embodiment example of FIG. 3. Unlike the embodiment example of FIG. 3, the tourniquet device 1 in the embodiment example of FIG. 4, however, does not comprise a compressor, but rather a connection 7' at a central gas supply, which makes available a compressed gas as a pressure means. A pressure reducer 8' and a valve 9' follow the pressure means connection 7'. The work pressure available after the pressure reducer 8' is detected by another pressure gauge 15.

The embodiment examples of tourniquet device 1 shown in FIGS. 2-4 have a detection mechanism via which the size or volume of the connected compression cuff 2 can be detected by means of a pressure measurement. To this end, during the operation of the detection mechanism, the compression cuff 2 connected at the connection 6 is first inflated over a prespecified detection period t1 using a first parameter set. The first parameter set corresponds thereby to the parameter set that is correlated to the smallest connectable compression cuff 2S of the cuff set. After the expiration of the detection period t1, the pressure produced in the connected compression cuff 2 is detected by means of the pressure gauge 13. If a two-chamber cuff or two individual cuffs are connected at the tourniquet device 1, the chamber pressure built up during the inflation of the two chambers a, b can be detected separately in each chamber a, b by means of the pressure gauges 13a and 13b. One can make a conclusion as to the size and, in particular, the volume of the connected cuff from the detected cuff pressure that has built up after the expiration of the detection period t1 in the compression cuff 2.

If the detected cuff pressure in the connected compression cuff 2 is above a prespecified first minimal pressure p1, then the connected compression cuff 2 is the smallest connectable cuff of the cuff set correlated to the tourniquet device 1. In this case, for the further inflation of the connected cuff, the control apparatus 4 of the tourniquet device 1 selects the parameter set that is correlated with the cuff with the smallest size or the smallest volume and further inflates the connected compression cuff 2 using this parameter set, over an inflation period t2, until the end pressure stipulated in accordance with this parameter set is attained.

If, on the other hand, the cuff pressure detected during the operation of the detection mechanism lies below the prespecified first minimal pressure p1, then from this, one can make a conclusion that not the smallest but rather a larger cuff (2M or 2L) is connected to the tourniquet device. In this case, the inflation apparatus 3 inflates the connected compression cuff 2 over a prespecified first inflation period t2, using a second parameter set that is provided for the second-smallest compression cuff (2M) of the cuff set. After expiration of the first inflation period t2, the cuff pressure built up in the connected compression cuff 2 is, in turn, detected by means of the pressure gauge 13. If the detected cuff pressure is above a second minimal pressure p2, which is larger than the first minimal pressure p1, then the connected compression cuff 2 is the second-smallest cuff of the cuff set. For the further inflation of the connected compression cuff 3, the control apparatus in this case then selects the parameter set that is correlated with this cuff with the second-smallest volume and inflates the connected cuff, using this parameter set, up to the prespecified end pressure. If the detected cuff pressure, on the other hand, lies below the second minimal pressure p2, it can then, on this basis, be concluded that the next-bigger compression cuff is connected to the tourniquet device 1. If the cuff set correlated with the tourniquet device 1 comprises, all total, three cuffs (2S, 2M, 2L) with different sizes (S, M, L), then the largest cuff (2L) of this cuff set is therefore connected in this case. In this case, the control apparatus then selects the parameter set correlated with the largest cuff for the further inflation of the connected cuff and inflates the connected cuff, in accordance with the inflation profile of this parameter set, up to the prespecified end pressure.

Figure 5:
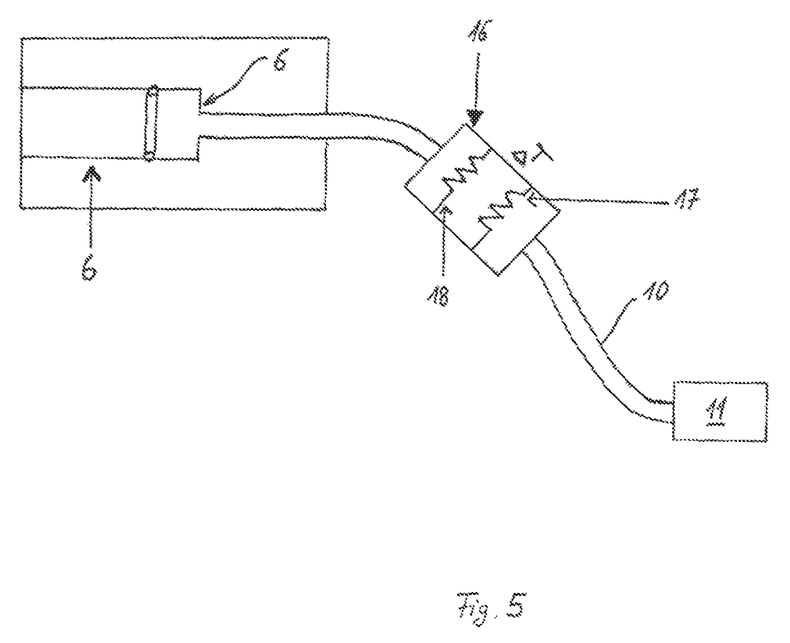
FIG. 5: schematic depiction of a detection mechanism for the detection of the cuff size or the volume of a compression cuff by means of a flow rate measurement.

FIG. 5 shows another embodiment of a tourniquet device with a detection mechanism for the detection of the connected compression cuff. In this embodiment example, the detection of the size or the volume of the compression cuff connected to the tourniquet device is carried out via a flow rate measurement. To this end, a flow rate gauge 16 is located in the pressure means conduit 10 between the proportional valve 11 and the connection 6. The flow rate gauge 16 detects the quantity of the pressure means flowing to the connection 6 through the pressure means conduit 10. From the quantity flowing through per unit time, one can make a conclusion as to the volume of the compression cuff (which is likewise not shown in FIG. 6) connected to the connection 6, by means of a connecting hose that is not shown.

The flow rate gauge 16 can, for example, be designed as a calorimetric or thermal flow rate gauge. The flow rate gauge 16 shown in FIG. 6 comprises a first resistance wire 17 and a second resistance wire 18, which act as temperature sensors. The first resistance wire 17 is thereby impinged first with a constant electric current, wherein it is heated and, in comparison to the other resistance wire 18, which detects the actual temperature in the pressure means conduit 10, produces a prespecified temperature difference $\Delta T$ when no pressure means flows through the pressure means conduit 10. If the pressure means (compressed gas), on the other hand, flows through the pressure means conduit 10, heat is removed from the heated resistance wire 17 by the gas flowing by and conducted away by the flow. The cooling that thereby results is detected and offset by the subsequent regulation of the heating current conducted through the first resistance wire 17 until the predefined temperature difference $\Delta T$ is reset. The subsequent regulation of the heating current is thus a measure for the cooling of the first resistance wire 17 by the gas flowing by, which, in turn, is directly proportional to the quantity of the gas flowing by. From the value of the subsequent regulation of the heating current, it is thus possible to make a conclusion as to the mass flow of the gas which has flowed through per unit time in the pressure means conduit.

In this way, the flow rate gauge 16 detects the mass flow of the pressure means flowing to the connection 6 through the pressure means conduit 10. Since this is dependent on the volume of the compression cuff connected to the connection 6, one can make a conclusion as to the volume of the compression cuff by means of the detection of the mass flow that goes into the connected compression cuff per unit time.

The control system in accordance with the invention, with the detection mechanism for the detection of the size or the volume of the compression cuff 2 connected to the tourniquet device 1, guarantees that the individually connected compression cuff is always inflated with the inflation profile that is correlated with it.

This prevents, on the one hand, a defective functioning and, in particular, an excessively strong inflation of a small compression cuff. Furthermore, the control system in accordance with the invention makes possible a quick inflation of the connected compression cuff, if its size is taken into consideration during the inflation and an inflation profile adapted to the cuff size can be used. Finally, harm to the tissue in the limb of the patient can also be avoided if the applied compression cuff is inflated with an inflation profile adapted and optimized with respect to the cuff size.

The invention is not limited to the described embodiment example. Thus, for example, the cuff set can comprise more than three compression cuffs with different sizes. In this case, the detection mechanism for the detection of the cuff size via a pressure measurement is then iteratively repeated if one of the larger cuffs of the cuff set is to be connected. The compression cuffs can be "dual-port" cuffs, which, in addition to a first pressure means connection for the inflation of the cuff, have a second connection for the detection of the cuff pressure.

The invention claimed is:

1. A tourniquet system for controllably inflating a connected compression cuff coupled to the tourniquet system, the connected compression cuff selected from a plurality of compatible compression cuffs, each of the compatible compression cuffs accommodating a different volume of compressed gas and coupleable to the tourniquet system, the tourniquet system comprising:
   an inflation apparatus for inflating the connected compression cuff;
   a control apparatus coupled to the inflation apparatus, the control apparatus configured for controlling the inflation apparatus for inflation of the connected compression cuff by determining inflation parameters of the connected compression cuff with a pressure measurement and using the determined inflation parameters of the connected compression cuff to control the inflation apparatus, the control apparatus having:
      a data storage unit storing inflation parameters for each compatible compression cuff of the plurality of compatible compression cuffs, the inflation parameters correlated to the volume of compressed gas accommodated by each compatible compression cuff of the plurality of compatible compression cuffs;
      detection means for detecting the volume of compressed gas accommodated by the connected compression cuff; and
      determining means for determining the volume of the connected compression cuff,
   wherein during operation of the tourniquet system the inflation apparatus inflates the connected compression cuff for a predetermined period of time according to the inflation parameters for the compatible compression cuff accommodating a smallest volume of compressed gas, the detection means detects pressure in the connected compression cuff after inflation for the predetermined period of time and transmits a pressure value detected to the determining means, and the determining means determines the volume of the connected compression cuff from the pressure value detected.

2. The tourniquet system according to claim 1, wherein the detection means is configured for detecting pressure by detecting pressure directly within the connected compression cuff or indirectly by detecting a flow rate of compressed gas from the inflation apparatus into the connected compression cuff.

3. The tourniquet system according to claim 1, wherein, during operation of the tourniquet system, if the pressure value detected exceeds a predetermined minimal pressure for the compression cuff accommodating a smallest volume of compressed gas, the inflation apparatus is configured for inflating the connected compression cuff until an end pressure of the compression cuff accommodating the smallest volume of compressed gas is attained.

4. The tourniquet system according to claim 1, wherein, during operation of the tourniquet system, if the pressure value detected is below a predetermined minimal pressure for the compression cuff accommodating a smallest volume of compressed gas, the inflation apparatus is configured for inflating the connected compression cuff for a predetermined period of time according to the inflation parameters for the compression cuff accommodating a second-smallest volume of compressed gas.

5. The tourniquet system according to claim 1, wherein the inflation parameters for each compatible compression cuff of the plurality of compatible compression cuffs include a time-dependent inflation profile for inflation of the compatible compression cuff.

6. The tourniquet system according to claim 1, wherein the inflation parameters for each compatible compression cuff of the plurality of compatible compression cuffs include a time-dependent pressure curve of an inflation process for inflation of the compatible compression cuff.

7. The tourniquet system according to claim 6, wherein the inflation parameters for each compatible compression cuff of the plurality of compatible compression cuffs include a time-dependent pressure curve of a discharge process for deflation of the compatible compression cuff.

8. The tourniquet system according to claim 1, wherein the inflation parameters for each compatible compression cuff of the plurality of compatible compression cuffs include a value for a maximum pressure over which the compatible compression cuff may not be inflated.

9. The tourniquet system according to claim 1, wherein the inflation parameters for each compatible compression cuff of the plurality of compatible compression cuffs include a value for a maximum period of time over which the compression cuff in inflated form may not exceed.

10. A tourniquet system for controllably inflating a connected compression cuff coupled to the tourniquet system, the connected compression cuff selected from a plurality of compatible compression cuffs, each of the compatible compression cuffs accommodating a different volume of compressed gas and coupleable to the tourniquet system, the tourniquet system comprising:

an inflation apparatus for inflating the connected compression cuff;
a control apparatus coupled to the inflation apparatus, the control apparatus configured for controlling the inflation apparatus for inflation of the connected compression cuff by determining inflation parameters of the connected compression cuff solely with a pressure measurement and using the determined inflation parameters of the connected compression cuff to control the inflation apparatus, the control apparatus having:
a data storage unit storing inflation parameters for each compatible compression cuff of the plurality of compatible compression cuffs, the inflation parameters correlated to the volume of compressed gas accommodated by each compatible compression cuff of the plurality of compatible compression cuffs;
detection means for detecting the volume of compressed gas accommodated by the connected compression cuff solely from a pressure measurement; and
determining means for determining the volume of the connected compression cuff,
wherein during operation of the tourniquet system the inflation apparatus inflates the connected compression cuff for a predetermined period of time according to the inflation parameters for the compatible compression cuff accommodating a smallest volume of compressed gas, the detection means detects pressure in the connected compression cuff after inflation for the predetermined period of time and transmits a pressure value detected to the determining means, and the determining means determines the volume of the connected compression cuff solely from the pressure value detected; and
wherein, during operation of the tourniquet system, if the pressure value detected is below a predetermined minimal pressure for the compression cuff accommodating a smallest volume of compressed gas, the inflation apparatus is configured for inflating the connected compression cuff for a predetermined period of time according to the inflation parameters for the compression cuff accommodating a second-smallest volume of compressed gas.

* * * * *